United States Patent
Shahbazi et al.

(10) Patent No.: US 9,892,816 B2
(45) Date of Patent: Feb. 13, 2018

(54) PLATINUM CONTAINING CONDUCTIVE PASTE

(71) Applicants: Samson Shahbazi, Roslyn, PA (US); Steven Grabey, Hazleton, PA (US); Mark Challingsworth, Glenside, PA (US)

(72) Inventors: Samson Shahbazi, Roslyn, PA (US); Steven Grabey, Hazleton, PA (US); Mark Challingsworth, Glenside, PA (US)

(73) Assignee: Heraeus Precious Metals North America Conshohocken LLC, West Conshohocken, PA (US)

(*) Notice: Subject to any disclaimer, the term of this patent is extended or adjusted under 35 U.S.C. 154(b) by 0 days.

(21) Appl. No.: 14/269,518

(22) Filed: May 5, 2014

(65) Prior Publication Data
US 2015/0004359 A1 Jan. 1, 2015

Related U.S. Application Data

(60) Provisional application No. 61/840,068, filed on Jun. 27, 2013.

(51) Int. Cl.
*B32B 3/24* (2006.01)
*B32B 18/00* (2006.01)
(Continued)

(52) U.S. Cl.
CPC .............. *H01B 1/16* (2013.01); *A61L 31/022* (2013.01); *A61L 31/026* (2013.01); *A61L 31/18* (2013.01);
(Continued)

(58) Field of Classification Search
None
See application file for complete search history.

(56) References Cited

U.S. PATENT DOCUMENTS 2,247,400 A * 7/1941 Palmer ............... C09F 1/00
530/211
2,300,433 A * 11/1942 Palmer ............... C09F 1/00
530/211
(Continued)

FOREIGN PATENT DOCUMENTS

EP 0 905 775 3/1999
EP 1 788 616 5/2007
(Continued)

OTHER PUBLICATIONS

Machine Translation of JP 05334911 A, Dec. 1993.*
Machine Translation of JP 09137066 A, May 1997.*
Machine Translation of JP 11242913 A, Sep. 1999.*

*Primary Examiner* — Jeff Vonch
(74) *Attorney, Agent, or Firm* — Blank Rome LLP; Francine F. Li

(57) ABSTRACT

An electroconductive hole plug paste comprising about 60-80 wt % of platinum particles, about 10-20 wt % of $Al_2O_3$, and about 10-20 wt % of organic vehicle, based upon 100% total weight of the paste, wherein the organic vehicle includes at least one viscosity-modifying component in an amount sufficient to provide the electroconductive hole plug paste with a viscosity of about 800-1,500 kcPs, is provided. A ceramic substrate assembly for an implantable medical device having the electroconductive hole plug paste of the invention, and a method of forming the same, are also provided.

22 Claims, 2 Drawing Sheets

(51) Int. Cl.

| | |
|---|---|
| B32B 37/06 | (2006.01) |
| B32B 38/04 | (2006.01) |
| A61N 1/05 | (2006.01) |
| H01B 1/14 | (2006.01) |
| H01B 1/22 | (2006.01) |
| H01B 1/16 | (2006.01) |
| C04B 41/45 | (2006.01) |
| C08L 1/28 | (2006.01) |
| A61L 31/02 | (2006.01) |
| A61L 31/18 | (2006.01) |
| H05K 3/40 | (2006.01) |
| H05K 3/46 | (2006.01) |
| H01L 23/498 | (2006.01) |

(52) U.S. Cl.
CPC .......... *A61N 1/05* (2013.01); *C04B 41/4501* (2013.01); *C04B 41/4576* (2013.01); *C08L 1/28* (2013.01); *H01B 1/22* (2013.01); *Y10T 428/24273* (2015.01); *Y10T 428/24322* (2015.01)

(56) References Cited

U.S. PATENT DOCUMENTS

| | | | | |
|---|---|---|---|---|
| 2,453,214 A * | 11/1948 | Figdor | ............... | C08L 1/28 106/178.1 |
| 3,158,503 A * | 11/1964 | Young | ............... | H05K 3/4053 118/301 |
| 3,536,508 A * | 10/1970 | Short | ............... | H01B 1/16 106/178.1 |
| 3,561,110 A * | 2/1971 | Feulner | ............... | H05K 3/102 156/89.16 |
| 4,409,135 A * | 10/1983 | Akimune | ............... | C04B 41/5177 106/1.15 |
| 4,552,691 A * | 11/1985 | Shoji | ............... | C04B 41/5127 106/1.18 |
| 4,636,332 A * | 1/1987 | Craig | ............... | C03C 3/062 252/514 |
| 5,283,104 A * | 2/1994 | Aoude | ............... | H01B 1/16 257/E23.075 |
| 5,344,592 A * | 9/1994 | Wilczek | ............... | B23K 35/3612 252/512 |
| 5,422,190 A * | 6/1995 | Alexander | ............... | C22C 32/0021 252/514 |
| 5,443,786 A * | 8/1995 | Yokoyama | ............... | H01B 1/02 252/512 |
| 5,496,619 A * | 3/1996 | Itagaki | ............... | H01L 23/49883 174/137 B |
| 5,601,638 A * | 2/1997 | Fukuda | ............... | H01L 23/49883 106/1.18 |
| 5,698,015 A * | 12/1997 | Mohri | ............... | H01L 23/49883 106/1.14 |
| 5,855,995 A * | 1/1999 | Haq | ............... | A61N 1/02 174/256 |
| 5,951,917 A * | 9/1999 | Nayak | ............... | H01B 1/22 252/500 |
| 6,042,751 A * | 3/2000 | Chan | ............... | G01N 27/3271 204/292 |
| 6,117,367 A | 9/2000 | Bezama et al. | | |
| 6,146,743 A * | 11/2000 | Haq | ............... | A61N 1/02 174/257 |
| 6,165,247 A * | 12/2000 | Kodas | ............... | B01J 2/003 257/E21.304 |
| 6,335,077 B1 * | 1/2002 | Tani | ............... | H01L 21/486 106/1.18 |
| 8,043,454 B1 * | 10/2011 | Jiang | ............... | H01L 23/15 156/89.11 |
| 2002/0139556 A1 * | 10/2002 | Ok | ............... | H01L 21/486 174/50.6 |
| 2004/0217455 A1 * | 11/2004 | Shiono | ............... | H01L 21/486 257/678 |
| 2007/0060970 A1 * | 3/2007 | Burdon | ............... | A61N 1/3754 607/37 |
| 2007/0113952 A1 * | 5/2007 | Nair | ............... | H01L 23/49883 156/89.11 |
| 2008/0268637 A1 * | 10/2008 | Inaba | ............... | H01B 1/22 438/660 |
| 2008/0314502 A1 * | 12/2008 | Ok | ............... | H05K 3/4061 156/89.16 |
| 2008/0314865 A1 * | 12/2008 | Ok | ............... | H05K 3/4623 216/17 |
| 2009/0107707 A1 * | 4/2009 | Yamakawa | ............... | H05K 1/092 174/257 |
| 2012/0321805 A1 * | 12/2012 | Takahashi | ............... | H05K 1/092 427/383.5 |
| 2013/0003257 A1 * | 1/2013 | Kim | ............... | H01B 1/22 361/321.4 |
| 2013/0004659 A1 * | 1/2013 | Glicksman | ............... | C22C 32/0021 427/125 |
| 2013/0032382 A1 * | 2/2013 | Morioka | ............... | A61N 1/3754 174/255 |
| 2013/0109986 A1 | 5/2013 | Liu et al. | | |
| 2013/0110212 A1 | 5/2013 | Feng et al. | | |
| 2013/0184797 A1 * | 7/2013 | Tang | ............... | A61N 1/3754 607/116 |
| 2014/0124713 A1 * | 5/2014 | Majumdar | ............... | H01B 1/22 252/513 |

FOREIGN PATENT DOCUMENTS

| | | | | |
|---|---|---|---|---|
| JP | 49122513 A | * | 11/1974 | |
| JP | 55002766 A | * | 1/1980 | |
| JP | 60046949 A | * | 3/1985 | |
| JP | 05334911 A | * | 12/1993 | |
| JP | 08148028 A | * | 6/1996 | |
| JP | 09137066 A | * | 5/1997 | |
| JP | 11241103 A | * | 9/1999 | |
| JP | 11242913 A | * | 9/1999 | |
| JP | 2004186339 A | * | 7/2004 | |
| JP | 2004319706 A | * | 11/2004 | |
| JP | 2006193796 A | * | 7/2006 | |
| JP | 2006202503 A | * | 8/2006 | |
| JP | 2006302848 A | * | 11/2006 | |
| JP | 2008227364 A | * | 9/2008 | |
| JP | 2008277766 A | * | 11/2008 | |
| SU | 684025 A | * | 9/1979 | |

* cited by examiner

PLATINUM CONTAINING CONDUCTIVE PASTE

TECHNICAL FIELD

The invention relates to a platinum-containing conductive paste. Specifically, the paste is useful as a hole plug paste for ceramic substrates of implantable medical devices. The platinum-containing paste is conductive and creates a hermetic seal that allows electrical current to flow to and from a device implanted in the body without contamination from (or contamination of) the bodily environment.

BACKGROUND

Implantable electrical medical devices, such as cardiac pacemakers, defibrillators, and neurostimulators, are intricately designed electrical devices used to regulate certain medical conditions. These devices are either permanently implanted into the human body, or are implanted and remain there for an extended period of time (typically many years). They must be able to withstand the harsh environmental conditions of the human body, and must be operable for a very long period of time without needing repair or replacement. Because they generate electrical signals, special considerations are taken into account when designing the circuitry, so as to maintain the integrity of the electrical connections between the power source, the electrodes, and the organ to which they are attached.

Conventional pacemakers, for example, are essentially comprised of two parts: the pacemaker "chamber" and the electrical leads. The chamber contains the power source (typically a battery), the circuitry that detects electrical signals emanating from the heart and returns electrical signals to the heart, and a timing device to regulate the patient's heartbeat. The leads are the conducting wires that carry the electrical signal from the chamber to the heart. Current pacemaker leads are typically platinum wires, having one end connected to the patient's heart and the other end connected to the circuitry in the pacemaker chamber. The wire is fed through a ceramic insulating substrate, for example an alumina-based substrate, within the chamber, and the connection site is then brazed with gold to create a hermetic seal.

U.S. Patent Publication Nos. 2013/0110212 and 2013/0109986 disclose a pacemaker assembly. The assembly includes a lead wire structure, which is attached at one end to a pulse generator and at the other end to an electrode head (which is ultimately attached to a human organ). The lead wire structure includes at least one sub-lead wire. The sub-lead wire includes a core wire, around which a carbon nanotube composite wire is wound. It is the core wire which conducts signals from the pulse generator to the human organ. According to at least one embodiment, the sub-lead core wire is formed of platinum.

Typically, the prior art devices require long manufacturing processing times and do not allow for easy changes to the configuration of the device during production. The structure of the leads and their connection to the ceramic substrate add to these disadvantages. Replacing the leads with a material that takes up less space than a solid wire would also allow these devices to be more compact, thus more efficient and comfortable for the patient. Lastly, as gaps are inevitably formed at the junction of the platinum wire and the ceramic substrate, gold brazing is required to form a hermetic seal. Not only is gold an expensive precious metal, but this brazing process requires an extra manufacturing step.

There is, therefore, a need for a conductive material which can replace the leads in implantable medical devices, while maintaining the requisite electrical properties, hermetic properties, and the ability to withstand the bodily environment without contaminating it.

SUMMARY

The invention provides an electroconductive hole plug paste having about 60-80 wt % of platinum particles, about 10-20 wt % $Al_2O_3$, and about 10-20 wt % of organic vehicle, based upon 100% total weight of the paste, wherein the organic vehicle includes at least one viscosity-modifying component in an amount sufficient to provide the electroconductive hole plug paste with a viscosity of about 800-1.500 kcPs.

The invention also provides a ceramic substrate assembly for an implantable medical device having a ceramic substrate having a front and back surface and at least one hole extending from the front surface to the back surface, and at least one hole plug formed within the at least one hole of the ceramic substrate, the at least one hole plug being formed of the electroconductive hole plug paste of the invention. The paste is typically fired in the assembly.

The invention also provides a ceramic substrate assembly for an implantable medical device having a plurality of stacked ceramic substrates each having a front and back surface and at least one hole extending from the front surface to the back surface, and at least one hole plug formed within the at least one hole of each of the plurality of stacked ceramic substrates, the at least one hole plug being formed of the electroconductive hole plug paste of the invention. The paste is typically fired in the assembly.

The invention further provides a method of forming a ceramic substrate assembly for an implantable medical device, including the steps of filling at least one hole in the ceramic substrate assembly with an electroconductive hole plug paste of the invention and firing the ceramic substrate assembly having the at least one hole filled with the electroconductive hole plug paste. Preferably, the ceramic substrate assembly is fired at a rate of about 0.5-1° C./minute from room temperature to a maximum temperature of about 1,300-1,800° C. to form at least one hole plug.

The method of forming a ceramic substrate assembly for an implantable medical device may further include, before the first step, the steps of providing a plurality of dried ceramic substrates each having a defined edge, stacking the plurality of dried ceramic substrates evenly along the defined edge to form a ceramic substrate assembly, laminating the ceramic substrate assembly, and forming the at least one hole vertically through the ceramic substrate assembly.

Other objects, advantages and salient features of the invention will become apparent from the following detailed description.

BRIEF DESCRIPTION OF DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
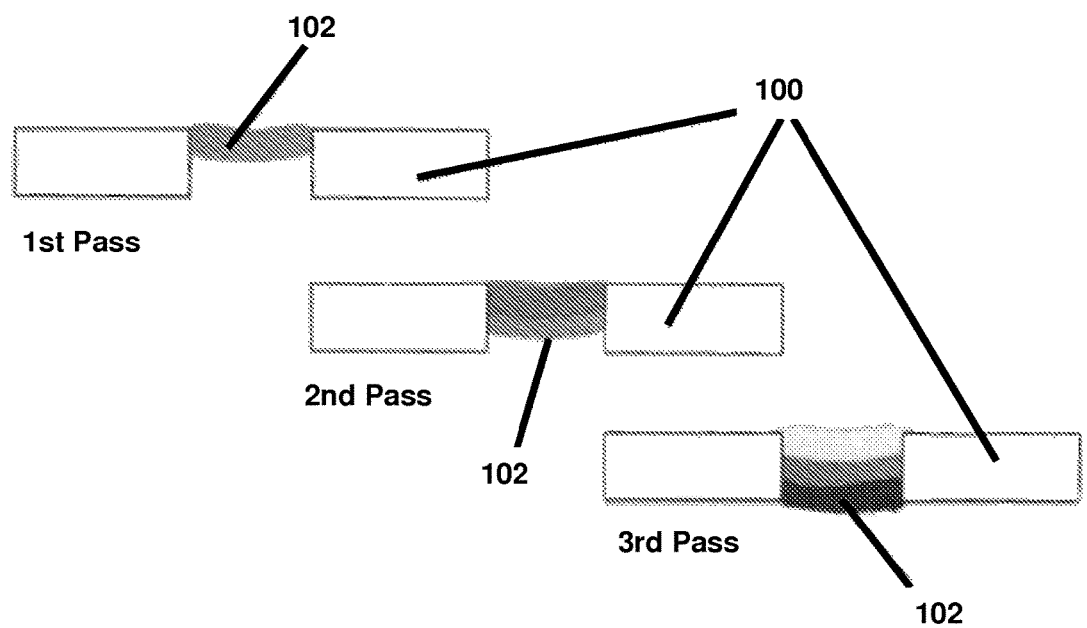
FIG. 1 is a cross-sectional view of a paste applied to a hole via stencil printing after a first, second and third pass.

The invention relates to an electroconductive paste useful to plug holes on ceramic substrates. Specifically, the electroconductive paste may be used as a hole plug paste on substrates incorporated into medical devices which are implanted into the human body. The electroconductive paste includes conductive particles containing platinum, alumina ($Al_2O_3$), and an organic vehicle.

Conductive Platinum Component

The platinum particles useful in the paste compositions described herein may be present as elemental platinum, one or more platinum compounds, or mixtures thereof. The platinum particles can exhibit a variety of shapes, surfaces, sizes, surface area to volume ratios, oxygen content and oxide layers. Examples of the variety of shapes include, but are not limited to, spherical, angular, elongated (rod or needle like) and flat (sheet like). Platinum particles may also be present as a combination of particles of different shapes. Platinum particles with a shape, or combination of shapes, which favors advantageous electrical conductivity of the produced hole plug are preferred. One way to characterize such shapes without considering their surface nature is through the following parameters: length, width and thickness. In the context of the invention, the length of a particle is given by the length of the longest spatial displacement vector, both endpoints of which are contained within the particle. The width of a particle is given by the length of the longest spatial displacement vector perpendicular to the length vector defined above both endpoints of which are contained within the particle.

While conductive particles may have an irregular shape, the particle size may be approximately represented as the diameter of the "equivalent sphere" which would give the same measurement result. Typically, particles in any given sample of platinum particles do not exist in a single size, but are distributed in a range of sizes, i.e., particle size distribution. One parameter characterizing particle size distribution is $D_{50}$. $D_{50}$ is the median diameter or the medium value of the particle size distribution. It is the value of the particle diameter at 50% in the cumulative distribution. Other parameters of particle size distribution are $D_{10}$, which represents the particle diameter at which 10% cumulative (from 0 to 100%) of the particles are smaller, and $D_{90}$, which represents the particle diameter at which 90% cumulative (from 0 to 100%) of the particles are smaller. Particle size distribution may be measured via laser diffraction, dynamic light scattering, imagine, electrophoretic light scattering, or any other methods known in the art.

In one embodiment, the platinum particles may have substantially uniform shapes. Specifically, the platinum particles may have shapes in which the ratios relating the length, the width and the thickness (i.e., length:width, length:thickness, and width:thickness) are close to 1, preferably all ratios lying in a range from about 0.7 to about 1.5, more preferably in a range from about 0.8 to about 1.3 and most preferably in a range from about 0.9 to about 1.2). For example, the platinum particles of this embodiment may be spheres, cubes, or a combination thereof, or combinations of one or more thereof with other shapes. In another embodiment, the platinum particles have a shape of low uniformity, preferably with at least one of the ratios relating the dimensions of length, width and thickness being above about 1.5, more preferably above about 3 and most preferably above about 5. Shapes according to this embodiment are flake shaped, rod or needle shaped, or a combination of flake shaped, rod or needle shaped with other shapes. In another embodiment, a combination of platinum particles with uniform shape and less uniform shape may be used. Specifically, a combination of spherical platinum particles and flake-shaped platinum particles, having different particle sizes may be used.

A variety of surface types of the platinum particles are known in the art. Surface types which favor effective sintering and yield advantageous electrical conductivity of the produced hole plug are favored according to the invention.

Another way to characterize the shape and surface of a platinum particle is by its surface area to volume ratio. i.e., specific surface area. The lowest value for the surface area to volume ratio of a particle is embodied by a sphere with a smooth surface. The less uniform and uneven a shape is, the higher its surface area to volume ratio will be. In one embodiment, the platinum particles have a high surface area to volume ratio, such as from about $1.0 \times 10^7$ to about $1.0 \times 10^9$ m$^{-1}$, from about $5.0 \times 10^7$ to about $5.0 \times 10^8$ m$^{-1}$ or from about $1.0 \times 10^8$ to about $5.0 \times 10^8$ m$^{-1}$. In another embodiment, the platinum particles have a low surface area to volume ratio, such as from about $6 \times 10^5$ to about $8.0 \times 10^6$ m$^{-1}$, from about $1.0 \times 10^6$ to about $6.0 \times 10^6$ m$^{-1}$ or from about $2.0 \times 10^6$ to about $4.0 \times 10^6$ m$^{-1}$. The surface area to volume ratio, or specific surface area, may be measured by BET (Brunauer-Emmett-Teller) method, which is known in the art.

The platinum particles may be present with a surface coating. Any such coating known in the art, and which is considered to be suitable in the context of the invention, may be employed on the platinum particles, such as, for example, oleic acid, stearic acid, neodecanoic acid, polymethacrylates, ammonium oleate, and polymeric surfactants. In one embodiment, the coating promotes better particle dispersion, which can lead to improved printing and sintering characteristics of the electroconductive paste. In certain embodiments, the coating is present in less than about 10 wt %, such as less than about 8 wt %, less than about 5 wt %, less than about 4 wt %, less than about 3 wt %, less than about 2 wt %, less than about 1 wt %, or less than about 0.5 wt %, based on 100% total weight of the platinum particles.

According to one embodiment, the electroconductive hole plug paste comprises about 60-80 wt % platinum particles, based upon 100% total weight of the paste. Preferably, the electroconductive hole plug paste comprises about 65-75 wt % platinum particles, and even more preferably, about 70-75 wt % platinum particles.

The Inorganic Component

The electroconductive hole plug paste of the invention may also include an inorganic component. The inorganic component acts as a filler and helps the electroconductive paste bond to the substrate. According to an aspect of the invention, the electroconductive paste includes $Al_2O_3$. Because the paste of the invention may be used in implantable medical devices, the $Al_2O_3$ preferably contains no impurities, such that it is at least 99.9% pure. In one embodiment, the electroconductive paste comprises about 10-20 wt % of $Al_2O_3$, based upon 100% total weight of the electroconductive paste. Preferably, the electroconductive paste includes 13-18 wt % $Al_2O_3$, and more preferably 15-17 wt % $Al_2O_3$, based upon 100% total weight of the electroconductive paste.

The inorganic component of the invention may be substantially lead free (e.g., containing less than about 5 wt %, such as less than about 4 wt %, less than about 3 wt %, less than about 2 wt %, less than about 1 wt %, less than about 0.5 wt %, less than about 0.1 wt %, or less than about 0.05 wt % or less than about 0.01 wt %) of lead, based upon 100% total weight of the inorganic component. In a preferred embodiment, the inorganic component is lead free (i.e., without any intentionally added lead or lead compound and having no more than 100 ppm of lead).

The inorganic component may be substantially amorphous, or may incorporate partially crystalline phases or compounds. The inorganic component may include a variety of other oxides or compounds (in addition to $Al_2O_3$) known in the art to be suitable for electroconductive pastes. For example, silicon, boron, aluminum, bismuth, zinc, titanium, chromium, germanium, vanadium, tungsten, molybdenum, niobium, tin, and indium compounds (e.g., oxides) may be used. Other compounds, such as alkaline and alkaline earth metal oxides (e.g., sodium, potassium, lithium, cesium, beryllium, calcium, strontium, and barium oxides), and rare earth oxides (e.g., lanthanum oxides and cerium oxides) may also be incorporated into the inorganic component to improve the electroconductive paste's hermetic properties. Because the electroconductive paste of the invention may be used in implantable medical devices, any additional oxides or compounds incorporated into the electroconductive paste should contain no impurities (i.e., the oxides or compounds should be at least 99.9% pure).

The inorganic component may be made by any process known in the art, including, but not limited to, mixing appropriate amounts of powders of the individual ingredients, heating the powder mixture in air or in an oxygen-containing atmosphere to form a melt, quenching the melt, grinding and ball milling the quenched material and screening the milled material to provide a powder with the desired particle size. For example, inorganic components, in powder form, may be mixed together in a V-comb blender. The mixture can be heated to around 800-1,300° C. (depending on the materials) for about 30-60 minutes. The materials can then be quenched, taking on a sand-like consistency. This coarse powder can be milled, such as in a ball mill or jet mill, until a fine powder results. Typically, the resulting powder is milled to an average particle size of about 0.01 to about 10 μm, preferably about 0.1 to about 5 μm.

The Organic Vehicle

Suitable organic vehicles that may be used in the pastes described herein are known to one of ordinary skilled in the art. In a preferred embodiment, the organic vehicle includes at least one viscosity-modifying component in an amount sufficient to provide the electroconductive hole plug paste with a viscosity of about 800-1,500 kcPs. According to one embodiment, the viscosity-modifying component provides the paste with a viscosity of about 1,000-1,500 kcPs. According to another embodiment, the viscosity-modifying component provides the paste with a viscosity of about 1,000-1,300 kcPs. The specific viscosity range is higher than the viscosity of most similar electroconductive pastes, as it allows the paste to be filled into holes on a ceramic substrate without flowing out.

In one embodiment, the organic vehicle comprises at least one binder and a solvent. The binder acts as the viscosity-modifying component. Preferably, the viscosity-modifying component includes ethyl cellulose and at least one thermoplastic resin derived from hydrogenated rosin. The electroconductive paste preferably includes about 6-8 wt % of ethyl cellulose and about 1-2 wt % of at least one thermoplastic resin derived from hydrogenated rosin, based upon 100% total weight of the paste. Other suitable binders include, but are not limited to, cellulose, phenolic, or acrylic resins. Suitable solvents include, but are not limited to, carbitol, terpineol, hexyl carbitol, texanol, butyl carbitol, butyl carbitol acetate, dimethyladipate or glycol ethers, or dipropylene glycol. The paste may comprise about 1-10 wt % of solvent, based upon 100% total weight of the paste. Preferably, the organic vehicle comprises binder(s) and solvent(s) that have low burnout temperatures (approximately 350° C. or lower) in order to reduce the char residue.

The organic vehicle may also optionally include additives, including surfactants and/or thixotropic agents. Suitable surfactants include, but are not limited to, polyethylene oxide, polyethylene glycol, benzotriazole, poly(ethylene glycol)acetic acid, lauric acid, oleic acid, capric acid, myristic acid, linolic acid, stearic acid, palmitic acid, stearate salts, palmitate salts, lecithin, and any combination of any of the foregoing. Suitable thixotropic agents include, but are not limited to, castor wax, oxidized polyethylene wax, amide wax, combination of amide and oxidized polyethylene wax, and any combination of any of the foregoing. The organic vehicle additives may be present in an amount of about 0-10 wt %, based upon 100% total weight of paste. In total, the electroconductive paste comprises about 10-20 wt % organic vehicle.

Formation of the Electroconductive Paste

The electroconductive paste compositions described herein may be prepared by any method for preparing a paste composition known in the art. The method of preparation is not critical, as long as it results in a homogeneously dispersed paste. As an example, without limitation, the paste components may be mixed, such as with a mixer, then passed through a three roll mill to make a dispersed uniform paste.

Formation of the Hole Plug in a Ceramic Substrate Assembly

As set forth herein, the electroconductive paste of the invention may be used to form hole plugs in a ceramic substrate assembly used in an implantable medical device. According to one embodiment of the invention, the ceramic substrate assembly includes a plurality of stacked ceramic substrates, such as "green" alumina-based tapes. According to another embodiment, the ceramic substrate assembly may include a single ceramic substrate. A "green" substrate is one which has been dried but not fired. While not limited to such an embodiment, each stacked tape layer may have a thickness of about 2-3 mil. Other suitable ceramic substrates include alumina/titania tapes, yttria-stabilized polycrystalline tetragonal zirconia (YTZP) tapes, or tapes made of hybrids of zirconia and alumina.

The ceramic substrates each have a front and back surface and are stacked on top of one another, such that the front surface of one substrate makes contact with the back surface of another substrate placed directly on top of it. The substrates also have a defined edge along which they are aligned when stacked, such that the ends of the substrates are flush with another. Once the ceramic substrates are stacked to a designated thickness to form the assembly, the assembly is laminated. To laminate, the assembly is placed in a press (an isostatic press or heat press) and heat and pressure are applied for a designated period of time to complete the lamination process. The parameters of the lamination process are specific to the type of tape used. Once laminated, the assembly is cleaned and at least one hole is formed through the thickness of the assembly. In this way, the hole(s) extend through each of the ceramic substrates, from the front surface to the back surface, and are vertically aligned. Specifically, the hole(s) may be formed via punching or drilling (abrasive drilling or laser drilling). If laser drilled, the holes should be free of slag and debris and are preferably further subjected to an annealing process. According to one embodiment, the hole(s) are approximately 5-15 mils in diameter.

The electroconductive paste of the invention, as described herein, is then applied to the hole(s) to form a hole plug. The paste may be applied according to any method known in the art, including, but not limited to, hand filling, stencil printing, injection printing, and bladder filling. A preferred method of applying the paste to the hole(s) is bladder filling. According to this process, an extrusion via filler (such as the VM08001 Via Fill System available from Pacific Trinetics Corporation of Los Alamitos, Calif.) is used. The processing parameters are input into the filler. Preferably, the clamp time is set at 6 seconds, the injection pressure is set at 40 psi, and the injection time is set at 4 seconds. A stainless steel stencil, having a thickness of 4-6 mils, is used. According to these set parameters, the extrusion via filler then fills the holes completely.

If a hand filling process is used, the paste is simply applied to the hole(s) by hand. At least 10-12 hand passes may be required to completely fill the hole(s). If stencil printing is used, a stencil (typically made of stainless steel) having a thickness of about 8 mils may be used. The recommended print speed is approximately 3 inches/second, with a squeegee durometer of 60. The process may be repeated about 4-6 times in order to completely fill the hole(s). In FIG. 1, the hole in the substrate 100 is completely filled with the electroconductive paste 102 via a stencil printing process in three passes, although more or less passes may be required depending on the properties of the paste and the depth of the hole.

Figure 2:
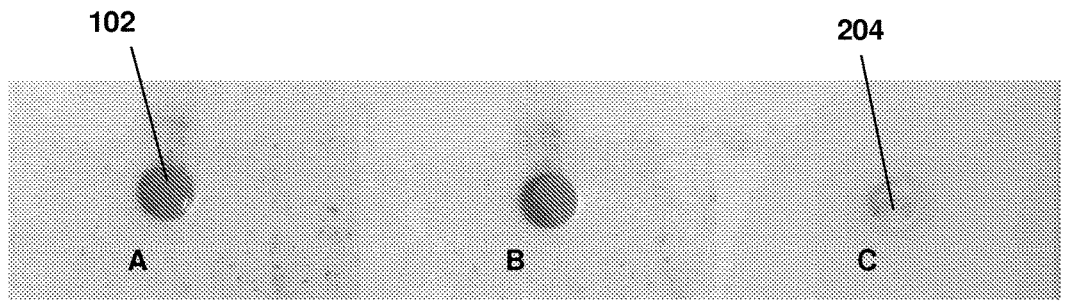
FIG. 2 is a top view of a conductive plug paste applied in a hole in a ceramic substrate according to an exemplary embodiment of the invention.

As depicted in FIG. 2, a hole having the applied electroconductive paste in "wet" form is shown in Step A. The electroconductive paste is then dried, as shown in Step B. In order to completely dry the paste, the assembly is heated to a temperature of about 150° C. for a period of about 10-15 minutes. The substrate is examined in both the wet and dried state under a microscope to ensure that the holes are properly filled before the substrate is fired. Lastly, the ceramic substrate assembly is co-fired together with the dried electroconductive paste. The assembly is heated from room temperature at a rate of about 0.5-1° C./minute to a maximum temperature of about 1,300-1,800° C. The temperature and time must be sufficient to sinter the platinum component of the electroconductive paste and burnout the organic phase. Upon completion of the firing stage, the fired electroconductive paste creates hole plug(s) within the ceramic substrate, as depicted in Step C. According to an embodiment of the invention, each hole plug exhibits an electrical resistance of about 200-300 mΩ. Further, the hole plug forms a hermetic seal with the ceramic substrate, which is advantageous for medical devices installed in the human body. The automatic seal which is created between the hole plug and the substrate is advantageous because no gold brazing is needed.

Figure 3:
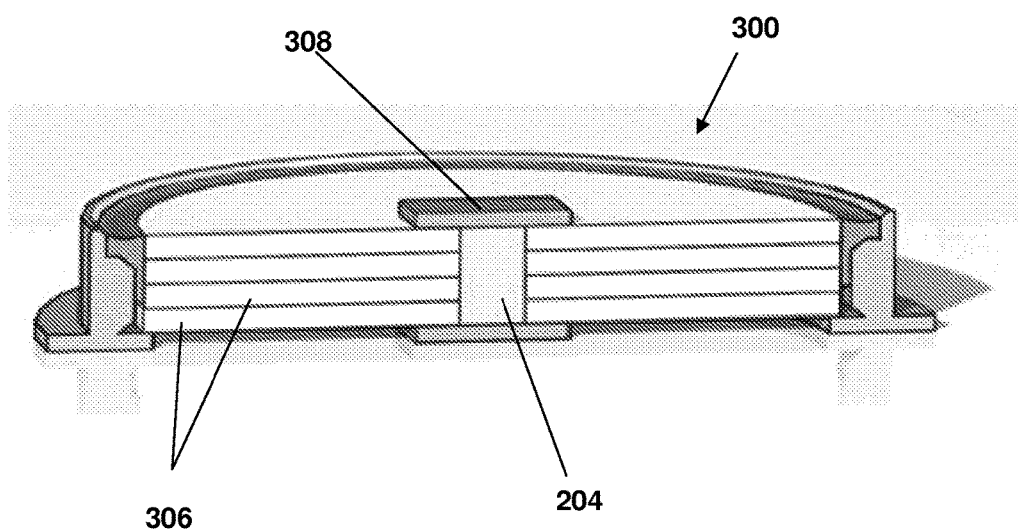
FIG. 3 is a cross-sectional view of an electrode of an implantable medical device having a conductive plug paste applied therein according to an exemplary embodiment of the invention.

As shown in FIG. 3, the completed ceramic substrate assembly 300 provides an electrical pathway through the hole plug 204. The hole plug 204 created by the fired electroconductive paste allows electricity to flow from one side of the assembly 300 to the other, while the ceramic substrate(s) 306 provide insulation so as to allow the electrical signal to flow only through the hole plug 204. Conductive pads 308 may be added to the outer surface of the assembly 300 so as to carry the electrical signal from the hole plug to another component of the medical device.

Performance Testing of Hole Plug

In order to determine whether a proper hermetic seal has been created, a red dye test can be performed. The red dye test involves placing a small droplet of red dye (such as Ely Checkmore 200 Red Dye Penetrant available from Matcon B.V. of The Netherlands) on the top of the hole plug and allowing it to sit for approximately 30 minutes. The opposite side of the hole plug is then checked to ensure that the red dye has not penetrated the hole and seeped through to the opposite side. If no red dye is visible, an acceptable hermetic seal has been formed. If red dye is visible, gaps are present between the hole plug and the ceramic substrate. Gaps can also be caused by improper firing profiles. At certain firing profiles, the electroconductive paste may shrink slower or faster than the ceramic substrate. If this occurs, gaps may form between the electroconductive paste in the hole and the ceramic substrate.

The hole plug may also be tested to ensure that it conducts electricity. A multimeter probe (such as the 34401A Digital Multimeter available from Agilent Technologies of Santa Clara, Calif.) is placed in contact with each side of the hole plug, and the device reads the electrical output. As set forth herein, according to the invention, each hole plug exhibits an electrical resistance of about 200-300 m.

EXAMPLE

The following example is given as a specific illustration of the invention. It should be understood, however, that the invention is not limited to the specific details set forth in the example.

An exemplary electroconductive paste was prepared with the following components: about 72 wt % platinum powder, having an average particle size ($D_{50}$) of about 10 μm, about 7 wt % ethyl cellulose, about 1.5 wt % of an ester of hydrogenated rosin, about 1 wt % polyacrylic acid, about 2.5 wt % of solvent and surfactant combined, and about 16 wt % pure $Al_2O_3$, having an average particle size ($D_{50}$) of about 2 μm, based upon 100% total weight of the paste. The polyacrylic acid was added to increase the tackiness of the paste, so as to facilitate its application into the ceramic substrate. The components of the paste were mixed until they reached a uniform consistency.

The exemplary paste was then applied to pre-formed holes in a ceramic substrate assembly comprising multiple stacked layers of a green alumina tape. The paste was applied via bladder filling. The ceramic substrate assembly, having the exemplary paste applied therein, was dried at 150° C. for a period of 15 minutes, and then fired at 0.5-1° C./minute, starting at room temperature and reaching a maximum temperature of 1700° C.

The hole plugs formed of the exemplary paste were then tested according to the parameters set forth above to determine whether they exhibited the requisite hermeticity and conductivity. The hole plug exhibited acceptable conductivity and had formed a complete hermetic seal.

These and other advantages of the invention will be apparent to those skilled in the art from the foregoing specification. Accordingly, it will be recognized by those skilled in the art that changes or modifications may be made to the above described embodiments without departing from the broad inventive concepts of the invention. Specific dimensions of any particular embodiment are described for illustration purposes only. It should therefore be understood that this invention is not limited to the particular embodiments described herein, but is intended to include all changes and modifications that are within the scope and spirit of the invention.

The invention claimed is:
1. A substrate assembly for an implantable medical device, comprising:
   at least one alumina substrate having a front and back surface and at least one hole extending from the front surface to the back surface
   a hole plug formed within the at least one hole of the alumina substrate, the hole plug being formed of an electroconductive hole plug paste including, prior to firing:
      about 60-80 wt % of platinum particles having substantially uniform shape, in which each of the ratios of length to width, length to thickness, and width to thickness of the platinum particles is about 0.7 to about 1.5;
      an inorganic component comprising about 10-20 wt % of Al2O3, wherein the inorganic component contains less than about 0.05 wt % of lead, based upon 100% total weight of the inorganic component; and
      about 10-20 wt % of organic vehicle, based upon 100% total weight of the paste, wherein the organic vehicle includes at least one viscosity-modifying component which comprises ethyl cellulose and at least one thermoplastic resin derived from a hydrogenated rosin.
2. The substrate assembly of claim 1, wherein the viscosity-modifying component includes about 6-8 wt % of ethyl cellulose and about 1-2 wt % of at least one thermoplastic resin derived from a hydrogenated rosin, based upon the total weight of the paste.
3. The substrate assembly of claim 1, wherein the organic vehicle has a burnout temperature of 350° C. or lower.
4. The substrate assembly according to claim 1, wherein the ratio of length to width to thickness of the platinum particles is about 0.8 to about 1.3.
5. The substrate assembly according to claim 4, wherein the ratio of length to width to thickness of the platinum particles is about 0.9 to about 1.2.
6. The substrate assembly according to claim 5, wherein the ratio of length to width to thickness of the platinum particles is about 1.
7. The substrate assembly of claim 1, wherein the inorganic component contains less than about 0.01 wt % of lead based upon 100% total weight of the inorganic component.
8. The substrate assembly of claim 7, wherein the inorganic component is lead free.
9. The substrate assembly according to claim 1, wherein the substrate assembly comprises a plurality of stacked alumina substrates.
10. The substrate assembly according to claim 9, wherein the at least one hole of each of the plurality of stacked alumina substrates are vertically aligned.
11. The substrate assembly according to claim 9, wherein the plurality of stacked alumina substrates are formed of alumina tape.
12. The substrate assembly according to claim 9, wherein the electroconductive hole plug paste is applied to the at least one hole of each of the plurality of stacked alumina substrates via hand printing, bladder filling, or stencil printing.
13. The substrate assembly according to claim 9, wherein the at least one hole is approximately 5-15 mils in diameter.
14. The substrate assembly according to claim 9, wherein the electroconductive hole plug paste within the at least one hole of each of the plurality of alumina substrates is co-fired with the plurality of alumina substrates that it forms the hole plug, the hole plug creating a hermetic seal.
15. The substrate assembly according to claim 9, wherein the hole plug has an electrical resistance of 200-300 mΩ.
16. A method of forming a substrate assembly for an implantable medical device, comprising the steps of:
   providing at least one alumina substrate having a front and back surface and at least one hole extending from the front surface to the back surface,
   filling the at least one hole in the at least one alumina substrate with an electroconductive hole plug paste, the an electroconductive hole plug paste including:
      about 60-80 wt % of platinum particles having substantially uniform shape, in which each of the ratios of length to width, length to thickness, and width to thickness of the platinum particles is about 0.7 to about 1.5;
      an inorganic component comprising about 10-20 wt % of Al2O3, wherein the inorganic component contains less than about 0.05 wt % of lead, based upon 100% total weight of the inorganic component; and
      about 10-20 wt % of organic vehicle, based upon 100% total weight of the paste, wherein the organic vehicle includes at least one viscosity-modifying component which comprises ethyl cellulose and at least one thermoplastic resin derived from a hydrogenated rosin; and
   firing the at least one alumina substrate having the at least one hole filled with the electroconductive hole plug paste to form a hole plug.
17. The method of forming the substrate assembly according to claim 16, wherein the at least one alumina substrate is a plurality of dried alumina substrates each having a defined edge, the first step further comprising the steps of:
   stacking the plurality of dried alumina substrates evenly along their defined edges to form the substrate assembly;
   laminating the substrate assembly; and
   forming at least one hole vertically through the substrate assembly.
18. The method of forming the substrate assembly according to claim 17, wherein the plurality of dried alumina substrates are formed of alumina tape.
19. The method of forming the substrate assembly according to claim 16, wherein the substrate assembly is fired at a rate of about 0.5-1° C./min from room temperature to a maximum temperature of about 1,300-1800° C.
20. The method of forming substrate assembly according to claim 16, wherein the hole plug has an electrical resistance of 200-300 mΩ.
21. The method of forming the substrate assembly according to claim 16, wherein the filling step is done via hand printing, bladder filling, or stencil printing.
22. The method of forming the substrate assembly according to claim 16, wherein the hole plug creates a hermetic seal.

* * * * *